United States Patent [19]

Juge et al.

[11] Patent Number: 5,043,465

[45] Date of Patent: Aug. 27, 1991

[54] ORGANIC PHOSPHORUS COMPOUNDS COMPLEXED TO BORON, THEIR PREPARATION AND APPLICATIONS

[75] Inventors: Sylvain Juge, Orsay; Jean-Pierre Genet, Fontenay-aus-Roses, both of France

[73] Assignee: Societe Nationale Elf Aquitaine, France

[21] Appl. No.: 458,496

[22] Filed: Dec. 28, 1989

[30] Foreign Application Priority Data

Jun. 30, 1989 [FR] France .................... 89 08763

[51] Int. Cl.⁵ .................................. C07F 9/02
[52] U.S. Cl. ............................ 558/72; 558/81; 558/84; 558/85
[58] Field of Search ............................... 558/72

[56] References Cited

PUBLICATIONS

Vaude Griend, "Structure–Basicity Relation . . .", J. Am. Chem. Soc. 99(8) 2459–63 (1977).

*Primary Examiner*—C. Warren Ivy
*Assistant Examiner*—Celia Chang
*Attorney, Agent, or Firm*—Ostrolenk, Faber, Gerb & Soffen

[57] ABSTRACT

New organic phosphorus compounds, comprised of hetero-phosphacycloalkanes whose phosphorus atom forms a complex with a borane. They can be prepared by the action of a borane on a hetero-phosphacycloalkane, within a solvent, at temperatures ranging from −20° to +60° C. Their transformation into other derivatives, phosphinites or phosphines in particular, can be carried out without any modification in the chirality of the initial complex. An especially useful application is their conversion into highly optically active phosphines, used in particular as catalysts in various reactions.

11 Claims, No Drawings

ORGANIC PHOSPHORUS COMPOUNDS COMPLEXED TO BORON, THEIR PREPARATION AND APPLICATIONS the invention relates to a series of new organic phosphorus compounds, complexed to boron on the P atom, and a process for preparing such compounds. More especially, it relates to hetero-phospha-cycloalkanes, notably dioxaphospholanes and oxazaphospholidines, whose phosphorus atom forms a complex with a borane. This invention also includes the application of new complexes in the preparation of various organic derivatives of phosphorus, in particular, phosphinites, phosphines, diphosphinites, diphosphines and similar compounds, complexed to boron and industrially useful. It is particularly advantageous for the preparation of such compounds with a stable chirality, for example having a high enantiomeric excess.

It is known that compounds such as phosphinites, phosphines, amino-phosphines, phosphine-oxides, etc. and their dicompounds can be used to synthesize various organophosphorated substances and are used in the preparation of catalysts including P ligands with organic groups. Phosphines are advantageously used in catalytic systems, for example, to carry out hydrogenation in a homogeneous medium. Such asymmetric hydrogenations have been described in the case of C=C groups and in the case of various ketones, notably by R. NOYORI et al. in J. Am. Chem. Soc. 1987, 109 p. 5856-5858, as well as by M. KITAMURA et al. in the same journal in 1988, 110, p. 629-631. Phosphines are also used in the preparation of metal-based catalysts, for hydroformylation and polymerization reactions, or in the isomerization of unsaturated hydrocarbons with ruthenium and phosphorus complexes. The advantage of phosphine-boranes in the preparation of certain catalysts that are very useful in asymmetric hydrogenation was disclosed by TSUNEO INAMOTO et al. in J. Am. Chem. Soc. 1985, 107, p. 5301-5303.

The new compounds according to the invention have the following general formula:

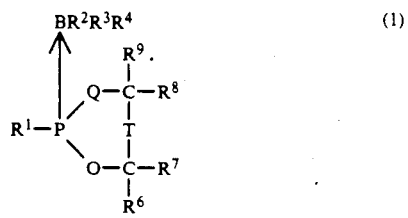
(1)

wherein Q represents an oxygen atom or a nitrogenated group

wherein $R^5$ is H, or a hydrocarbon group, particularly a $C_1$ to $C_{12}$ alkyl or a $C_6$ to $C_{10}$ aryl; $R^1$ is a hydrogen atom, a halogen, an amino group, a hydroxyl, a $C_1$ to $C_{18}$ alkyl or alkenyl or/and a corresponding alkoxy, a $C_6$ to $C_{10}$ aryl, a phenoxy or cycloaliphatic group; $R^1$ can carry a second phosphorated group, similar to

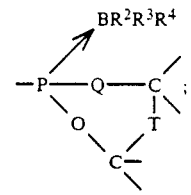

$R^2$, $R^3$ and $R^4$, similar or different, are H, $C_1$ to $C_6$ alkyls or/and $C_6$ to $C_{10}$ aryls; $R^6$ to $R^9$, similar or different, are H, halogens, OH, hydrocarbon, aliphatic, cycloaliphatic aryl or/and alkylaryl radicals; T represents a simple bond or a $C_1$ to $C_4$ alkylene which can constitute part of an aryl or cycloaliphatic ring.

When one or more of the $R^6$ to $R^9$ groups are hydrocarbon groups, it is preferable that they are $C_1$ to $C_{12}$ alkyls or alkenyls, $C_6$ to $C_{18}$ aryls, possibly substituted, cyclopentyls or/and cyclohexyls.

The case where $R^1$ carries a second phosphorated group is illustrated hereafter, in which case it is designated by $R^{10}$ whose definition is analogous to that of $R^1$, given hereinabove. Formula (2) thus represents a dicompound corresponding to monocompound (1).

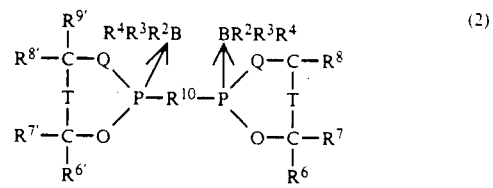
(2)

The general definition of groups $R^{6'}$ to $R^{9'}$ is the same as that for groups $R^6$ to $R^9$ but they may individually differ from the latter.

When Q is an oxygen atom, compounds (1) and (2) are derivatives of 1,3,2-dioxaphospholane; if Q is a nitrogenated group

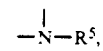

these compounds are derivatives of 1,3,2-oxazaphospholidine; in both cases, the presence of borane complexed to phosphorus leads to a number of remarkable advantages, notably that bodies (1) or (2) can be easily transformed into stable borane complexes of phosophines, phosphinites, or their derivatives, extremely useful as catalysts of various reactions, allowing compounds with the desired chirality to be selectively obtained.

The simplest products, according to formula (1) or (2), most currently used according to the invention are, in the form of $R^1$, $R^6$ to $R^9$, or $R^{6'}$ to $R^{9'}$, $C_1$ to $C_4$ alkyls or/and phenyls or methylphenyls, $R^{10}$ being a $C_1$ to $C_4$ alkylene or a phenylene, and $R^2$ to $R^4$ being H, whereas T is a singlebond or —CH$_2$—; of practical use also is compound (1) wherein $R^1$ is a —N=dialkyl whose alkyl has 1 to 3 carbon atoms, and a compound (2) wherein $R^{10}$ is

whose alkyl has 1 to 3 carbon atoms.

The process according to the invention is characterized in that a boron compound $BR^2R^3R^4$ whose definition is given hereinabove is reacted, within a solvent, with a hetero-phospha-cycloalkane at a temperature ranging from $-20°$ to $+60°$ C. and preferably from $0°$ to $40°$ C.

Dioxaphospholanes and oxazaphospholidines having the formula given below are particularly suitable as hetero-phospha-cycloalkanes:

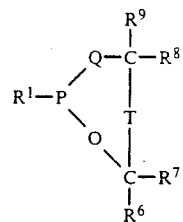

(3)

wherein the symbols Q, $R^1$, T and $R^6$ to $R^9$ have the same meaning as in formula (1) described hereinabove. The corresponding dicompound, analogous to that in formula (2), without $BR^2R^3R^4$, can also be used.

The preferred proportions range from 1 to 2 moles of borane $BR^2R^3R^4$ per mole of compound (3).

Various suitable solvents can be used, especially tetrahydrofurane, benzene, toluene, etc., depending on the solubility of the products used. Hetero-phospha-cycloalkane concentration can vary depending on the kind of hetero-phospha-cycloalkane used but it is preferably about 0.1 to 1M and particularly 0.3 to 0.7M.

A good procedure consists in stirring the reaction mixture, generally for 1 to 10 hours, most often for 2 to 6 hours, followed by bubbling an inert gas, particularly nitrogen, and evaporation of the solvent. Depending on the case in question, the yield of borane complex can exceed 90%, generally ranging from 35 to 95%. This facility in obtaining complexes according to the invention is quite unexpected as, according to the prior art (Tsuneo IMAMOTO mentioned hereinabove), it was necessary to work in the presence of a reducing agent and a $CeCl_3$ catalyst in order to form a borane complex of phosphine. It is surprising to find that, according to the invention, such complexes can be formed quite easily, without a reducing agent or a catalyst, as long as a hetero-phospha-cycloalkane is used to start with rather than a phosphine or phosphinite. Therefore, as borane complexes, according to the invention, can be easily transformed into the corresponding complexes of phosphines, phosphinites or their derivatives, the invention provides an unexpected means for obtaining these different complexes.

Thus, the present invention includes the application of the new compounds (1) and (2) to the preparation of various phosphinites and phosphines complexed by boranes; it is particularly applicable to the production of optically active complexes of phosphinites, phosphines, amino-phosphines, phosphine oxides, diphosphinites, diphosphines and phosphine dioxides. One of its important advantages is that the chirality of starting compound (1) or (2) is entirely preserved throughout the course of these applications, thus allowing the desired optical activity to be obtained in the final product.

One application of complexes (1) and (2) is their transformation into phosphinites by the opening of the alkane ring by means of an organo-metallic compound $R_n^{11}M$, $R^{11}$ being an alkyl or alkylene, generally a $C_1$ to $C_{12}$ alkyl or alkylene, a $C_6$ to $C_{10}$ aryl or a cycloalkyl, whereas n refers to the valency of metal M which can be, for example, Li, Mg, Zn, Al or another metal easily giving rise to organo-metallic derivatives. The organo-metallic compound formed is then hydrolyzed; the group of reactions taking place can be outlined as follows:

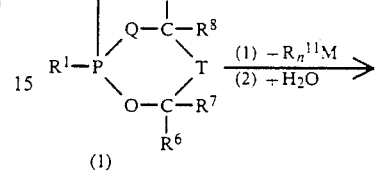

(4)

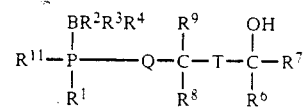

Ring opening preferably takes place between $-100°$ and $+25°$ C. Similarly, the dicompound corresponding to (4) is obtained on starting with the dicompound according to the invention (2) and double the amount of $R_n^{11}M$.

Starting with compound (4) or its dicompound, having the desired optical activity, various industrially useful derivatives can be obtained by conventional reactions, such as, for example, acid splitting, alcoholysis, amination, etc.

For example, $R^{12}OH$ acid alcoholysis of body (4), whose Q is

gives:

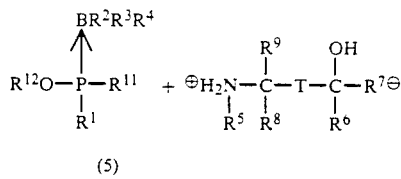

(5)

($R^{12}$ being an alkyl, preferably a $C_1$ to $C_{12}$ alkyl, or an aryl, more especially a $C_6$ to $C_{10}$ aryl). Thus, the asymmetric inductor (5) can be recovered without loss of chirality. Furthermore, this phosphinite (5) can be transformed into the corresponding phosphine-borane (6) by the action of an organo-metallic compound $MR^{13}$:

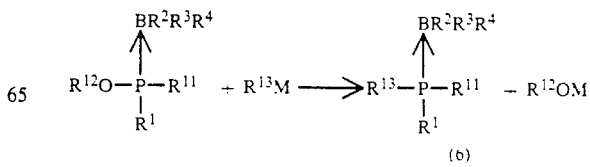

(6)

This demonstrates one of the many possibilities offered by the new complexes (1) and (2) according to the invention.

Still another application consists in treating the intermediate product (4) with a hydracid HX, which gives:

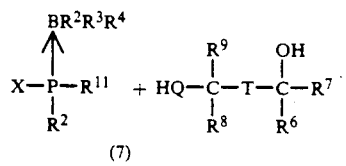

(7)

The optical activity of the halogeno-phosphine (7) is then a function of of the concentration of the acid HX used. The asymmetric inductor is recovered without loss of chirality.

An important application of the invention resides in the preparation of chiral phosphines having high optical purity whose enantiomeric excess (ee) can be close to 100%. The usefulness of such phosphines prompted many researchers to conceive different methods for their preparation. Thus, various publications on the subjcet are found such as those, for example, of: K. MISLOW—J.A.C.S. 4842 (1968) and 7009 (1969); M. MIKOLAJCZYK—Pure and Appl. Chem. 52, 959 (1980); W. CHODKIEWICZ—J. Organomet. Chem. 273 (1984)—C 55; S. JUGE patents FR—2518 100 and 2 537 143; T. KOIZUMI—Tetrahedron Letters 22, p. 571 (1981); W. J. RICHTER J. Organomet. Chem. 301, 289 (1986); T. IMAMOTO—Tetrahedron Letters 26, p. 783 (1985) and J. of Synth. Org. Chem. Japan 592; SUGA and JUGE—Chem. Letters p. 913 (1983) and p. 1915 (1987). Starting with a dichlorophosphine, namely Ph-PCl$_2$, or a phosphine oxide, these known methods generally have a number of drawbacks, the most frequent of which is the necessity of separating diastereoisomers and deoxygenating phosphine oxide, the limitation in nature of hydrocarbon groups on phosphorus, frequently low yields and the difficulty in obtaining sufficient optical purity.

Therefore, the use of hetero-phospha-cyclanes complexed to a borane according to the invention presents a number of unexpected advantages: yields can reach 70 to 100% and enantiomeric excesses ee are close or equal to 100%; the remarkable stability of borane complexes makes it possible to carry out each step in the preparation without preliminary separation of the product formed in the previous step; this considerably simplifies the task and improves yields. Moreover, it should be noted that the borane complexes of the hetero-phospha-cyclanes used are very easily obtained from standard dihalogeno-phosphines and secondary amines, followed by the action of an amino-alcohol, ephedrine for example, which is quantitatively recovered during the course of preparation and can consequently be re-used in another preparation.

Given the importance of this aspect of the invention, the chain of reactions leading to a chiral phosphine starting with Ph—PCl$_2$ as a raw material is given hereinafter. It is to be understood that specific compounds (A) to (I), mentioned here, are merely illustrative and are not to be construed as being restrictive as the process can be carried out with the different hetero-phospha-cycloalkane-boranes defined at the beginning of the present description.

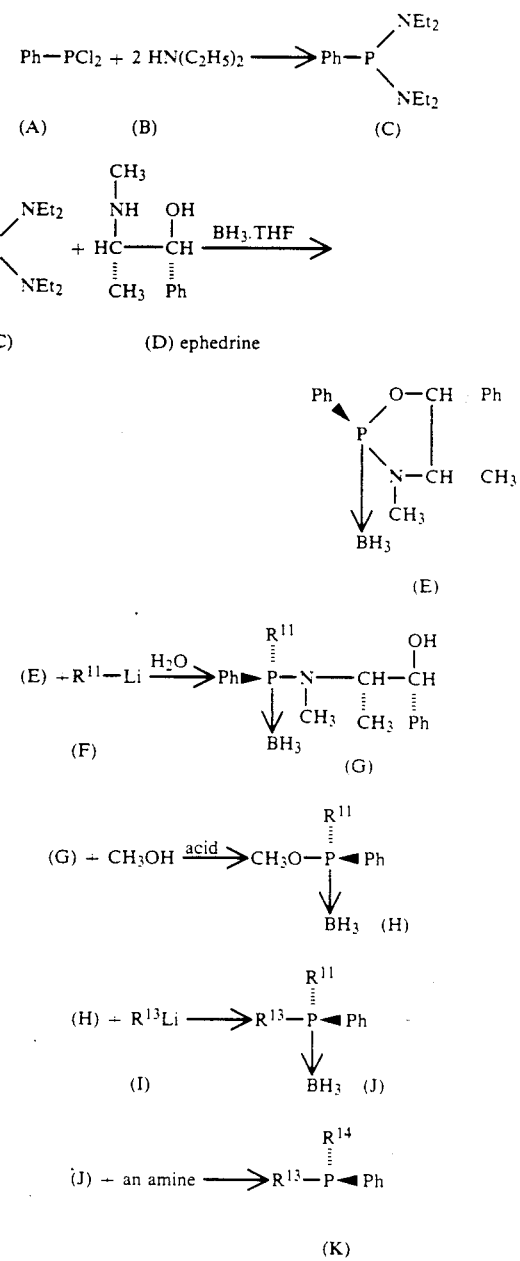

The reactions take place in an analogous manner if a borane complex of di-(hetero-phospha-cyclane), according to formula (2) given hereinbefore, is used to start with, rather than with the monocompound (E) of the diagram hereinabove. This leads to, for example, a phosphine of the type:

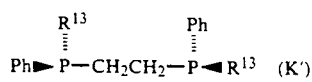

It should also be noted that when a given amount of phosphinite (H) has been prepared, it can be used to produce any of the chiral phosphines desired, using R$_{13}$ Li (I) whose R$^{13}$ radical can vary quite considerably: it can be, for example, a methyl, ethyl, propyl, isopropyl, butyl, isobutyl, hexyl, decyl, dodecyl, phenyl, tolyl, xylyl, cumenyl, mesityl, benzyl, phenethyl, cyclopentyl, cyclohexyl, naphthyl, etc. A wide choice is also possible relative to radical $R^{11}$ in the organometal (F) used to open the borane complex (E) ring to give the intermediate (G).

Furthermore, alcoholysis of (G) into the phosophinite (H) quantitatively releases without loss of optical activity the amino-alcohol (D) used, in particular ephedrine, which was used to obtain the starting complex (E). This chiral amino-alcohol can thus be advantageously recycled, as mentioned hereinabove.

The invention allows as many R or S isomers as required of the desired phosphine to be obtained; for this, the order in which R'and $R^2$ groups are introduced can be reversed, i.e. (I) is used instead of (F) and vice versa, or a (+) or (−) amino-alcohol can be reacted in (D).

Preparation according to the outline given hereinabove can also be carried out with a diol instead of (D), for example, 1,1-diphenylpropan-1,2-diol, $$CH_3\text{---}CH\text{---}\underset{\underset{Ph}{|}}{\overset{\overset{OH}{|}}{C}}\text{---}Ph$$
$$\phantom{CH_3\text{---}CH\text{---}}\overset{OH}{|}$$

It is important to note the exceptional behaviour of borane complexes according to the invention. In fact, when acid alcoholysis is carried out with a $W(CO)_5$ complex, according to the reaction (G)+$CH_3OH\rightarrow$ (H) of the outline given above, phosphinous acid and phosphinite are essentially obtained:

$$Ph\blacktriangleright\underset{\underset{W(CO)_5}{\Big\downarrow}}{\overset{\overset{CH_3}{\vdots}}{P}}\text{---}\underset{\underset{CH_3}{|}}{N}\text{---}\underset{\underset{CH_3}{\vdots}}{CH}\text{---}\underset{\underset{Ph}{\vdots}}{\overset{\overset{OH}{|}}{CH}} + CH_3OH \xrightarrow{\text{acid}\atop SO_4H_2}$$

$$HO\blacktriangleright\underset{\underset{W(CO)_5}{\Big\downarrow}}{\overset{\overset{CH_3}{\vdots}}{P}}\text{---}Ph + CH_3O\blacktriangleright\underset{\underset{W(CO)_5}{\Big\downarrow}}{\overset{\overset{CH_3}{\vdots}}{P}}\text{---}Ph$$

Yield: 80% ... 20%
ee = 54%

The transformation of these complexes into phosphine is difficult. On the other hand, the analogous procedure with borane complex (G) gives:

$$Ph\blacktriangleright\underset{\underset{BH_3}{\Big\uparrow}}{\overset{\overset{CH_3}{\vdots}}{P}}\text{---}OCH_3 + \underset{\underset{CH_3}{\vdots}}{HC}\text{---}\underset{\underset{Ph}{\blacktriangle}}{\overset{\overset{CH_3\text{---}\overset{\oplus}{N}H_2}{|}}{CH}}.SO_4H^{\ominus}$$
(H)            (D) ephedrine Yield: 95% ... 95%
ee = 96%

The examples which follow illustrate the invention without in any way limiting it. The different heterophospha-cycloalkanes, which were used in the preparation of the complexes according to the invention, were obtained using known methods, in particular those described in the publications of French patent no. 2562 543 and 2 564 842, as well as in the doctorate thesis (Orsay University) of Y. LEGRAS dated June 5, 1984 that of S. JUGE dated Oct. 16, 1984.

EXAMPLE 1

Preparation of (−) (2,5-dimethyl-4,4-diphenyl-1,3,2-dioxaphospholane)-borane (2R, 5S)

200 ml of a 0.5M 2,5-dimethyl-4,4-diphenyl-1,3,2-dioxaphospholane solution in tetrahydrofurane (THF) are introduced into a flask equipped with a magnetic stirrer and a nitrogen inlet. 100 ml of 1M $BH_3$ solution in THF is slowly added to the above solution at 20° C., with stirring. After 4 hours' stirring, nitrogen is bubbled through the mixture formed for a period of 1 hour. The solvent is then evaporated. The residue obtained is chromatographied on silica with toluene as the eluant. The colorless, non crystallized product has the following characteristics.

$$\underset{BH_3}{\overset{CH_3}{\diagdown}}\overset{}{\underset{\diagup}{P}}\underset{O\text{---}CH\text{---}CH_3}{\overset{O\text{---}\overset{\overset{Ph}{|}}{C}\text{---}Ph}{\diagup}}$$

$[\alpha]_D = -270°$ (c = 2 in $CHCl_3$).
$H^1$NMR ($CDCl_3$) δ:= 1.18 (3,d, J = 6.5); 1.26 (3,d, J = 7.5); 5.48 (1,m, $J_1$ = 6.5, $J_2$ = 8.5); 7.2-7.35 (5,m); 7.35-7.5 (5,m).
$C^{13}$NMR ($CDCl_3$) δ:= 17.9 (d,J = 27); 19 (d.J = 4.5); 81.08 (d,J = 5).
$P^{31}$NMR ($CDCl_3$) δ:= +172.4 ppm; IR (pure) ($cm^{-1}$) = 2400; 860-1000.

| % | Analysis: $C_{16}H_{20}BO_2P$ | |
|---|---|---|
| | C | H |
| calculated | 71.1 | 7.4 |
| found | 69.9 | 7.4 |

Mass 226 (5): 194 base peak.

EXAMPLE 2

Preparation of (4,4'-diphenyl-2-ethyl-5-methyl-1,3,2-dioxaphospholane)-borane (2R, 5S)

In the procedure of example 1, the dioxaphospholane used was replaced with the same proportion of 4,4'-diphenyl-2-ethyl-5-methyl-1,3,2-dioxaphospholane.

The characteristics of the white crystalline product obtained are as follows.

$$\underset{BH_3}{\overset{C_2H_5}{\diagdown}}\overset{}{\underset{\diagup}{P}}\underset{O\text{---}CH\text{---}CH_3}{\overset{O\text{---}\overset{\overset{Ph}{|}}{C}\text{---}Ph}{\diagup}}$$

Melting point = 110°-111° C., $[\alpha]_D = -226°$ (c = 1.2 in $CHCl_3$).
$H^1$NMR ($CDCl_3$): o = 1.02 (3,d.t. $J_1$ = 8, $J_2$ = 18); 1.19 (3,d, J = 6); 1.46 (2,m); 5.34 (1,P, $J_1$ = 6, $J_2$ = 7); 7.2-7.35 (5,m); 7.35-7.5 (5,m).
$C^{13}$NMR ($CDCl_3$): o = 6.13; 19.2 (d, J = 5); 24.8 (d, J = 27); 81.3 (d, J = 5.5); 91.9 (d).

P³¹NMR (CDCl₃): $\delta = +177.5$ ppm (q, $J_{PB}=88$).
IR (KBr): (cm⁻¹)=2400–2430; 975.

| Analysis: $C_{17}H_{20}BO_2P$ | | |
|---|---|---|
| % | C | H |
| calculated | 68.0 | 7.3 |
| found | 68.1 | 7.4 |

Mass 242 (1): 194 base peak; 179 (25); 165 (25); 115 (43).

EXAMPLE 3

Preparation of (−) (5-methyl-2,4,4-triphenyl-1,3,2-dioxaphospholane)-borane (2R, 5S)

The same technique as above is used, the dioxaphospholane used being (−) (5-methyl-2,4,4-triphenyl-1,3,2-dioxaphospholane). The following complex is obtained

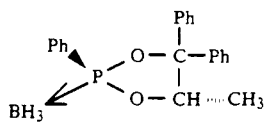

in the form of a white crystalline product with the following characteristics.

Melting point = 158° C.; $[\alpha]_D^{20} = -104°$ (c = 6 in CHCl₃).

H¹NMR (CDCl₃): $\delta = 1.24$ (3,d, J=6.5); 5.12 (1,d.q. $J_1=4$, $J_2=6.5$); 7.2–7.5 (15,m).
C¹³NMR (CDCl₃): $\delta = 18.8$ (d, J=8); 80.7 (d, J=5.5).
C¹³NMR (CDCl₃): $\delta = +154.7$ ppm (q, $J_{PB}=87$).
IR (KBr): (cm⁻¹)=2400–2410; 1115–920, 1650–1270.

| Analysis: $C_{21}H_{22}BO_2P$ | | |
|---|---|---|
| % | C | H |
| calculated | 72.4 | 6.3 |

EXAMPLE 4

Preparation of (3,4-dimethyl-2,5-diphenyl-1,3,2-oxazaphospholidine)-borane (2R, 4S, 5R)

The same operating procedure as in the previous examples is applied to 3,4-dimethyl-2,5-diphenyl-1,3,2-oxazaphospholidine. A white crystalline product is thus obtained with a yield of 90%, melting at 110° C. and having the following formula

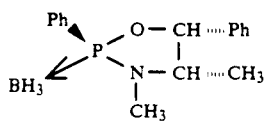

TLC silica-toluene: Rf value = 0.7.

| Analysis: $C_{16}H_{21}BNOP$ | | | |
|---|---|---|---|
| % | C | H | N |
| calculated | 67.3 | 7.4 | 4.9 |
| found | 67.5 | 7.5 | 4.9 |

IR (KBr): 2340–2360–2420 cm⁻¹, 1205-1180-1120-960 cm⁻¹.

| Mass: | 272 (45) | 118 (98) | 56 (51) |
|---|---|---|---|
| | 214 (18) | 108 (27) | |
| | 165 (base peak) | 91 (31) | |

P³¹NMR (CDCl₃): $\delta = +134.2$ (q, $J_{PB}=80$).
H¹NMR (CDCl₃): $\delta = 0.83$ (3,d, J=8), $\delta=2.7$ (3,d, J=11), $\delta=3.62$ (1,m), $\delta=9.65$ (1,d.d, $J_1=8$, $J_2=3$), $\delta=7.3$–8 (10, m).
C¹³NMR (CDCl₃): $\delta = 13.5$, $\delta=29.4$ d, J=9), $\delta=59$, $\delta=84.1$ (d, J=9).
$[\alpha]_D^{20} = +1.74$. (c = 4, CHCl₃).

EXAMPLE 5

Preparation of (2-phenyl-4,5-pinane-1,3,2-dioxaphospholane)-borane

The same procedure as in the previous examples is followed, the hetero-phospha-cycloalkane used being 2-phenyl-4,5-pinane-1,3,2-dioxaphospholane. The complex obtained

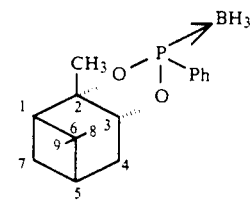

has the following characteristics.

P³¹NMR (CDCl₃): +152.7 ppm.
H¹NMR (CDCl₃): $\delta = 0.8$ 2.5 ppm (group-18H) of which 3 singlets at 0.85, 1.25 and 1.35 ppm each having an intensity of 3H; 4.5–4.75 (m, 1H); 7.2–7.9 (m, 5H).
IR (pure): $\bar{v}$ cm⁻¹ = 2400; 1520; 1460; 1380.

EXAMPLE 6

Application of the Product of Example 3 in the Preparation of a Phosphinite 3 ml of anhydrous THF containing 0.35 g (i.e. 1 mmole) of the complex prepared according to example 3 are introduced into a double-necked flask equipped with a cooler. 1 mmole of CH₃Li (i.e. 0.022 g) in the form of 0.625 ml of a 1.6M CH₃Li solution in anhydrous THF is added under nitrogen at a temperature of −78° C., the mixture being stirred magnetically. After 1 hour, 0.1 ml of water is added to the reaction mixture and stirring is continued for 1 hour, but at room temperature this time. At the end of this time, 25 ml of CH₂Cl₂ are added and the mixture is dried over Na₂SO₄. After filtration on "Millipore" (trade name), the solvent is evaporated and the residue is chromatographed on a 20×20 cm silica plate with toluene as the eluant.

A second series of similar operations were carried out with the sole exception of the reaction with CH₃Li being carried out at −100° C. instead of at −78° C.

In both cases, the following two isomers were obtained but in different proportions.

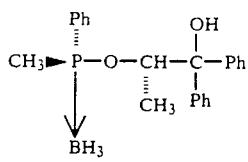   B

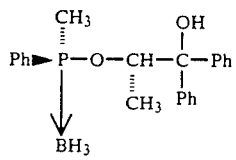   A

The relative proportions of the two isomers formed, depending on whether the reaction between the starting complex and CH3Li took place at −78° C. or at −100° C., are:

|  | A | B |  |
|---|---|---|---|
| −78° C. | 68% | 32% | Separable by re- |
| −100° C. | 98.3% | 1.7% | crystallization in cyclohexane |

It is thus possible to control the desired amount of compound A or B obtained by adjusting the temperature. These white, crystallized bodies have the following properties:

|  | A | B |
|---|---|---|
| Melting point | 143° C. | 163° C. |
| $[\alpha]_D^{20}$ | −3° | −5.9° |
|  | (c = 4.5/CHCl3) | (c = 1.5/CHCl3) |

They are useful as catalysts in the hydrogenation of carbonyl compounds.

EXAMPLE 7

Application of the Product of Example 3 after Transformation According to Example 6

The phosphinite isomer (A), obtained in example 6, was suspended in a 10% NaOH aqueous solution at a concentration of 0.1 g of this isomer per 10 ml of solution. The minimum amount of THF required to dissolve the product was added and the mixture was refluxed for 48 hours. The THF was then evaporated and the solution extracted with CH2Cl2 in order to eliminate the diol formed. After acidification, the aqueous solution is extracted with three times 50 ml of CH2Cl2. The organic phases are combined, dried and evaporated.

Hydrolysis of the phosphinite borane complex formed in example 6 thus resulted in the following compounds

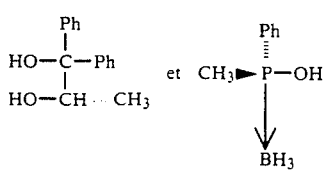

the first of which (diol) was eliminated using CH2Cl2, whereas the second compound collected, methyl phenyl phosphinite borane, was used as an interesting hydrogenation catalyst. This compound has the following characteristics:

Ir: $\bar{V}_{OH}=2500$; 3500 cm$^{-1}$; $\bar{V}_{BH}=2460$ cm$^{-1}$; $\bar{V}=1440$, 1150 cm$^{-1}$.

NMR: H$^1$ (250 MH2): δ=0.2-1.5 (m, 3H), δ=1.62 (d, 3H, H=1); 7.4-7.8 (m, 5H). P$^{31}$ (CDCl3): δ=+95.2 ppm.

EXAMPLE 8

Application of the Oxazaphospholidine Borane Complex Obtained According to Example 4

Following the technique described in example 6, i.e. CH3Li at −78° C. then hydrolysis, (3,4-dimethyl-2,5-diphenyl-1,3,2-oxazaphospholidine)-borane (2R, 4S, 5R) was converted into the corresponding amino-phosphine complex.

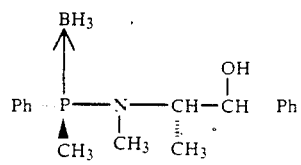

with a yield of 80%. White crystals. These bodies melt at 108° C.

| % | Analysis: C17H25BNOP | | |
|---|---|---|---|
|  | C | H | N |
| theory | 67.8 | 8.3 | 4.6 |
| found | 67.8 | 8.6 | 4.6 |

NMR P$^{31}$ (CDCl3): δ=+67 ppm.

H$^1$ (CDCl3): δ=1.20 (3, D, J=7), δ=4 (1, q, d, $J_1=J_2=7$, $J_{P-H}=11$), δ=1.49 (3, d, J=9), δ=4.68 (1, d, J=7).

C$^{13}$ (CDCl3): δ=11.2 (d, $J_{PC}=42$), δ=58 (d, $J_{PC}=8$).

This compound can be easily transformed into methyl phenyl chlorophosphine borane, from which it is then possible to obtain a whole series of different phosphines.

I—One operating procedure consists in dissolving 1 mmole of aminophosphine in 5 ml of CH2Cl2 and bubbling dry gaseous HCl through it until the white starting product disappears. The mixture is filtered and the solvent is evaporated.

The methyl phenyl chlorophosphine borane obtained

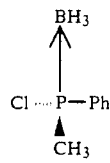

is a colorless oil which crystallizes without heating and which can be used without purification. It is obtained with a yield of 95%. A few of its characteristics are as follows:

$[\alpha]_D^{20}=+0.85°$ (C=13, CH2Cl2).

IR (pure): 2450, 1600, 1300, 1000, 905 cm$^{-1}$.

H$^1$NMR (CDCl3): δ=2.13 (3, d, J=8), δ=7.4-8.2 (5 m).

II—In a second operating procedure, the aminophosphine complex is dissolved in a minimum amount of toluene and the solution obtained is mixed with a solution of dry HCl in toluene. The hydrochlorate precipitate formed is eliminated by filtration. The methyl phenyl chlorophosphine borane solution in toluene is used without further treatment to prepare phosphines.

EXAMPLE 9

Preparation of the Borane Complex of Methyl Phenyl Methyl-Phosphonite

The methanolysis reaction is carried out on an amino-phosphine, an isomer of the amino-phosphine of in example 8:

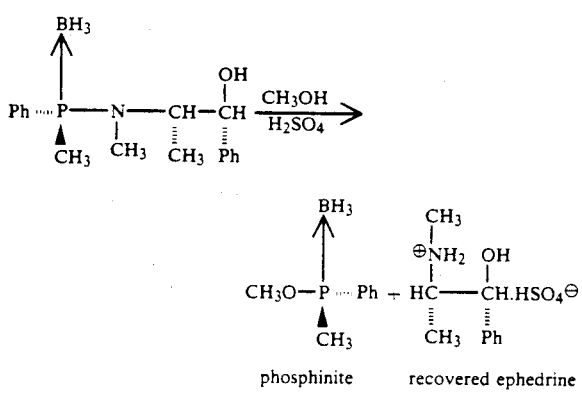

phosphinite    recovered ephedrine

A solution of 2 mmoles of the amino-phosphine above in 16 ml of dry methanol is placed in a 50 ml flask. 0.2 g of concentrated $H_2SO_4$ is added to this solution with stirring. After 1 hour, the reaction is stopped by the addition of 50 ml of water.

The methanol is then driven off by evaporation and the residue extracted by three times 20 ml of $CH_2Cl_2$. Evaporation of the extract solvent leaves the liquid phosphinite, which boils at 90° C. under 1 mmHg. Yield is 90%.

$[\alpha]_D^{20} = -104°$ (C=5 $CHCl_3$).

|  | Analysis: | |
|---|---|---|
|  | C | H |
| calculated | 57.14 | 8.37 |
| found | 57.03 | 8.33 |

IR (pure): $V_{BH}$ 2350 $cm^{-1}$
1430, 1400, 1050 $cm^{-1}$ $H^1$NMR: $\delta = 1.75$ (3H, d, J=10$H_2$), 3.65 (3H, d, J=13$H_2$), 7.3–8.1 (5H, m).

Mass: M-1 (5%), 154 (100%), 139 (50%), 123 (13%).

The aqueous phase resulting from decantation is neutralized with a 10% Na bicarbonate aqueous solution. It is extracted with ether or dichloroethane which leads to ephedrine to be quantitatively recovered without loss of optical activity.

EXAMPLES 10 to 12

Preparaton of Chiral Phosphines from Methyl Phosphinite Complexed to Borane

The reaction can be outlined as follows:

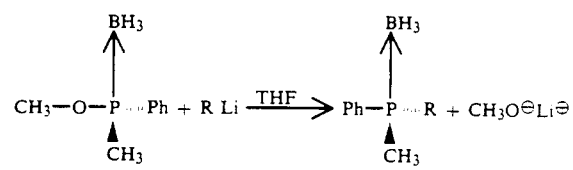

This reaction is repeated three times, varying the R group each time:
 example 10, R being ortho-anisyl,
 example 11, R being ortho-butoxy phenyl,
 example 12, R being n-butyl.

The operating procedure is the same in all three cases. 1 mmole of the phosphinite shown hereinabove is dissolved in 3 ml of dry THF, then 2 mmoles of R Li are added under nitrogen at −78° C. with stirring. The reaction is followed with TLC (silica; toluene/hexane).

After disappearance of the starting phosphinite, the reaction medium is hydrolyzed with 0.15 ml of water, the temperature being adjusted to 25° C. The initial THF is evaporated and 20 ml of water are added. The mixture is subjected to extraction with three times 20 ml of $CH_2Cl_2$. After drying the extracts thus obtained, the residue is comprised of pure phosphine borane, produced with yields of 91 to 93% in the three cases mentioned hereinabove.

HPLC analysis on a "CHIRACEL OK" column shows an enantiomeric excess ee of 95 to 97%.

The characteristics of the three phosphine boranes obtained are as follows.

| Example: | 10 | 11 | 12 |
|---|---|---|---|
| Formula | (ortho-OCH₃-phenyl)(Ph)P(CH₃)·BH₃ | (ortho-OC₄H₉-phenyl)(Ph)P(CH₃)·BH₃ | C₄H₉(Ph)P(CH₃)·BH₃ |
| $[\alpha]_D^{20}$ | = −25° | | = +9.8° |
| $H^1$NMR (CDCl₃) | δ = 0.94 (3,d, J=10.5) | 0.89 (3,4, J=7) | 0.9 (3,t, J=7) |
|  | δ = 3.7 (3,s) | 1.32 (2,m) | 1.2–1.5 (4,m) |
|  | δ = 6.85–8.2 (9,m) | 1.59 (2,m) | 1.5 (3,d, $J_{ph}$=10) |

Release of Phosphines from their Borane Complexes

A solution of 1 mmole of borane complex in 5 ml of diethylamine is introduced, under nitrogen, into a flask surmounted by a cooler. The solution is maintained at 50° C. for 12 hours. The diethylamine is then evaporated and the residue is taken up with 10 ml of hexane. A diethylamine-borane precipitate forms which is eliminated by filtration. The organic phase is washed three times with 10 ml of water. After drying and evaporation of the solvent, the pure phosphine is obtained with a yield of 91 to 94%.

The characteristics of the phosphines thus obtained starting with the complexes of examples 10 and 12 are as follows.

| Example 10 | Example 12 |
|---|---|
| o-anisyl methyl phenyl Phosphine ("PAMP") H'NMR (CDCl$_3$) | R(+)n-butyl methyl phenyl phosphine |
| $\delta = 1.62$ (3,d, J = 4) | $\delta = 0.8$ (3,t, J = 7) |
| $\delta = 3.83$ (3,s) | $\delta = 1.15$ (3,d, J = 4) |
| $\delta = 6.8-7.8$ (9,m) | $\delta = 1.33$ (6,m) |
| crystallizes without heating | oily consistency |

No change in chirality accompanies the transition from the borane complex to the phosphine itself.

EXAMPLE 13

Application of the Product of Example 3 After Transformation According to Example 6

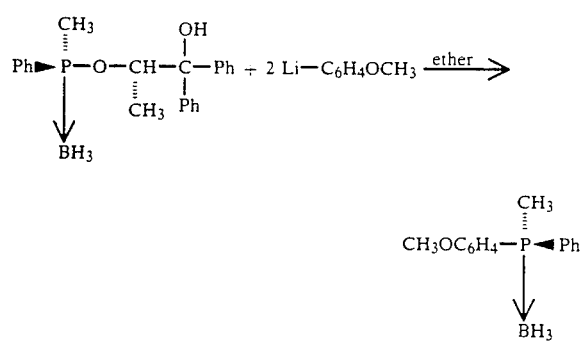

The main phosphinite isomer A, obtained in pure form in example 6, was dissolved in ether. 2 equivalents of o-anisyl lithium are added at −78° C. and the temperature is left to increase to 25° C. After being left for one night, the mixture is hydrolyzed, extracted and purified by chromatography on silica. This leads to o-anisyl methyl phenyl phosphine borane being obtained. This compound has the same characteristics as the compound in example 10, except that its configuration and rotatory power are reversed.

EXAMPLE 14

Application of the Oxazaphospholidine Borane Complex Obtained According to Example 4

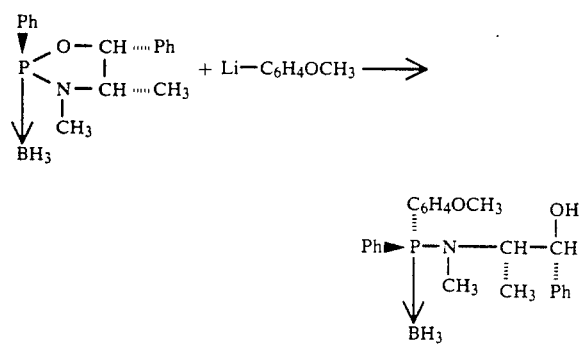

Following the technique described in example 6, i.e. using o-anisyl lithium at −78° C. then hydrolysis, (3,4-dimethyl-2,5-diphenyl-1,3,2-oxazaphospholidine)-borane (2S, 4R, 5R) was converted into the corresponding amino-phosphine with a yield of 90%.

| H NMR (CDCl$_3$) | P$^{31}$NMR (CDCl$_3$) +69.5 ppm |
|---|---|
| 3H(d) 1.2 ppm | |
| 1H(s) 2.1 ppm | $\overline{V}$ (IR) 2381 cm$^{-1}$ |
| 3H(d) 2.5 ppm | |
| 3H(s) 3.55 ppm | |
| 1H(m) 4.3 ppm | 1H(d) 4.8 ppm 9H(m) 6.8-7.7 ppm |

EXAMPLE 15

Preparation of the Borane Complex of O-Anisylphenyl Methyl Phosphinite

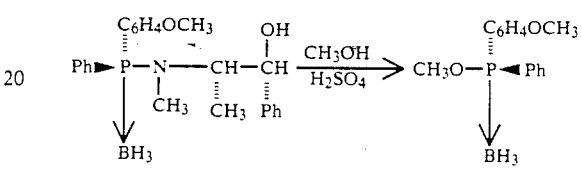

According to a procedure identical to that described in example 9, the complexed amino-phosphine of example 14 gives o-anisyl phenyl phosphinite with a yield of 95%:

$[\alpha]_D^{20} = -35.6°$ (C=2, CHCl$_3$).

| IR $\overline{v}$ = 2383 cm$^{-1}$ |
|---|
| BH |
| $v$ = 1035 cm$^{-1}$ |
| P—O |
| C—O |

P$^{31}$ NMR (CDCl$_3$) +107 ppm J$_{PB}$=81 H$_2$.

H$^1$ NMR (CDCl$_3$): 3H(m) 0.3-1.7 ppm, 3H(s) 3.6 ppm, 3H(d) 3.7 ppm, 9H(m) 6.8-7.7 ppm.

EXAMPLE 16

Preparation of Chiral Phosphines from the Methyl Phosphinite Complexed to Borane, Prepared in Example 15

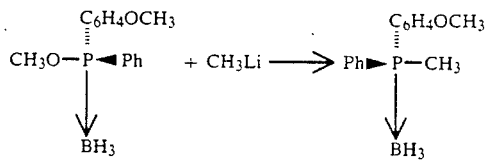

According to a procedure identical to that described in example 10, o-anisyl methyl phenyl phosphine borane is obtained with a yield of 90% by the action of methyl lithium on the o-anisyl phenyl phosphinite complex prepared according to example 15. In this case, the sign of the rotatory power and the configuration of the product obtained are reversed as the order in which o-anisyl and methyl groups were added to the starting complex was reversed.

We claim:

1. A boran complexed heterophosphacycloalkane of the formula

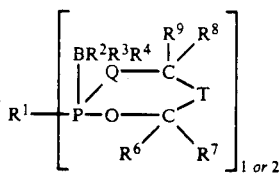

wherein
- Q is O or $NR^5$ in which $R^5$ is hydrogen or $C_{1-12}$ hydrocarbon;
- $R^2$, $R^3$ and $R^4$ are individually hydrogen, $C_{1-6}$ alkyl or $C_{6-10}$ aromatic hydrocarbon;
- $R^6$–$R^9$ are individually hydrogen, halogen, hydroxy or $C_{1-18}$ hydrocarbon;
- T represents a single bond or a $C_{1-4}$ alkylene which can constitute part of an aromatic hydrocarbon or cycloaliphatic ring; and
- $R^1$ is a monovalent or divalent moiety selected from the group of hydrogen, halogen, amino optionally substituted by $C_{1-3}$ alkyl, hydroxy, $C_{1-18}$ alkyl, $C_{1-18}$ alkenyl, $C_{1-18}$ alkoxy, $C_{6-10}$ aromatic hydrocarbon, $C_{1-4}$ alkylene, phenylene and $N(C_{1-3}$ alkyl).

2. A boran complexed hetero-phosphacycloalkane according to claim 1 in which the $R^6$ to $R^9$ groups are individually hydrogen, alkyl, alkenyl, aryl, cyclopentyl or cyclohexyl.

3. A boran complexed hetero-phosphacycloalkane according to claim 1 in which Q is $NR^5$.

4. A boran complexed hetero-phosphacycloalkane according to claim 3 in which at least 90% thereof is present in a single enantiomeric form.

5. A boran complexed hetero-phosphacycloalkane according to claim 1 in which Q is oxygen.

6. A boran complexed hetero-phosphacycloalkane according to claim 5 in which $R^1$ is a monovalent moiety selected from the group consisting of $C_{1-4}$ alkyl, phenyl and methylphenyl; $R^6$–$R^9$ are individually hydrogen, $C_{1-4}$ alkyl, phenyl or methylphenyl; $R^2$, $R^3$, and $R^4$ are hydrogen; and T is a bond or a —$CH_2$— group.

7. A boran complexed hetero-phosphacycloalkane according to claim 1 in which $R^1$ is —$N(C_{1-3}$ alkyl$)_2$ or —$N(C_{1-3}$ alkyl).

8. A boran complexed hetero-phosphacycloalkane according to claim 7 in which at least 90% thereof is present in a single enantiomeric form.

9. A boran complexed hetero-phosphacycloalkane according to claim 1 in which $R^1$ is a monovalent moiety selected from the group consisting of $C_{1-4}$ alkyl, phenyl and methylphenyl; $R^6$–$R^9$ are individually hydrogen, $C_{1-4}$ alkyl, phenyl or methylphenyl; $R^2$, $R^3$, and $R^4$ are hydrogen; and T is a bond or a —$CH_2$— group.

10. A boran complexed hetero-phosphacycloalkane according to claim 1 selected from the group consisting of (2,5-dimethyl-4,4-diphenyl-1,3,2-dioxaphospholane)-borane;
(4,4'-diphenyl-2-ethyl-5-methyl-1,3,2-dioxaphospholane)-borane;
(5-methyl-2,4,4-triphenyl-1,3,2-dioxaphospholane)-borane;
(3,4-dimethyl-2,5-diphenyl-1,3,2-oxazaphospholidine)-borane; and
(2-phenyl-4,5-pinane-1,3,2-dioxaphospholane)-borane.

11. A boran complexed hetero-phosphacycloalkane according to claim 1 in which at least 90% thereof is present in a single enantiomeric form.

* * * * *